United States Patent [19]

Andrieu et al.

[11] Patent Number: 5,523,094
[45] Date of Patent: Jun. 4, 1996

[54] TRANSDERMAL PHARMACEUTICAL COMPOSITION

[75] Inventors: Véronique Andrieu, Boulogne Billancourt; Louis Henrion, Boulogne; Jean Montel, Chatou; Alexander Wick, St. Nom la Bretèche, all of France

[73] Assignee: Synthelabo, Le Plessis-Robinson, France

[21] Appl. No.: 277,971

[22] Filed: Jul. 20, 1994

Related U.S. Application Data

[63] Continuation of Ser. No. 101,721, Aug. 4, 1993, abandoned.

[30] Foreign Application Priority Data

Aug. 5, 1992 [FR] France .................. 92 09711

[51] Int. Cl.$^6$ .......... A61K 9/70; A61K 31/505; A61K 31/19; A61K 31/045
[52] U.S. Cl. .......... 424/449; 514/258; 514/259; 514/260; 514/557; 514/724
[58] Field of Search .................. 514/258, 259, 514/260, 557, 724; 424/449

[56] References Cited

U.S. PATENT DOCUMENTS

| | | | |
|---|---|---|---|
| 3,742,951 | 7/1973 | Zaffaroni | 424/449 |
| 4,315,007 | 2/1982 | Manoury | 514/259 |
| 4,661,491 | 4/1987 | Regnier | 514/260 |

FOREIGN PATENT DOCUMENTS 2197589  5/1988  United Kingdom.

*Primary Examiner*—Marianne M. Cintins
*Assistant Examiner*—Kevin E. Weddington
*Attorney, Agent, or Firm*—Jacobson, Price, Holman & Stern

[57] ABSTRACT

A pharmaceutical preparation intended for transdermal administration contains alfusozin [(N-[3-[(4-amino-6,7-dimethoxy-2-quinazolinyl)methylamino]propyl]tetrahydro-2-furancarboxamide] or a salt thereof and a mixture composed of water, at least one organic solvent and at least one absorption promoter.

3 Claims, No Drawings

TRANSDERMAL PHARMACEUTICAL COMPOSITION

This application is a continuation application of Ser. No. 08/101,721, filed Aug. 4, 1993, now abandoned.

FIELD OF THE INVENTION

The invention relates to a transdermal pharmaceutical preparation containing, as active principle, N-[3-[(4-amino-6,7-dimethoxy-2-quinazolinyl)methylamino]propyl]tetrahydro-2-furancarboxamide (or alfuzosin) or a salt thereof formulated so as to make possible absorption of alfuzosin through the skin at a carefully chosen application site.

PRIOR ART

Alfuzosin is a known compound and is a selective antagonist of post-synaptic α-1-adrenergic receptors.

Alfuzosin shows a specificity for the α-1-adrenergic receptors situated in the vesical triangle of the urethra and in the prostate.

Alfuzosin, in the hydrochloride form, is used therapeutically for treating benign hypertrophy of the prostate. The therapeutic use of alfuzosin requires an administration which leads to plasma levels which are sufficient, steady over time and maintained for as long as possible.

Generally, for any medicament, a sharp rise in plasma level or a plasma peak which is too high brings about unfavourable effects. Plasma levels which are too low or non-continuous undermine the therapeutic effectiveness. This is why the search for satisfactory plasma levels sometimes leads to frequent oral administrations or to parenteral administrations which are unpopular, complex and expensive. In each case, discomfort ensues which undermines observance on the part of the patient.

In order to avoid these disadvantages of the oral and parenteral forms, the possibility of resorting to a transdermal administration has very often been examined. This type of administration produces plasma levels which are sufficient, steady, constant and sustained. Furthermore, administration is easy, daily or more spread out and easy to carry out for the patient and the doctor.

By their nature, different molecules are absorbed through human skin to greater or lesser extents. Several possibilities exist for making it easier for active molecules to pass through skin, such as modifying the permeability of the corneal layer, passing through the hair follicles or changing the state of the skin's surface.

Various chemical or physical means can also activate and facilitate the transdermal passage of molecules, for example the use of absorption promoters, electrical currents or sound waves.

Scientific works published to date make it clear that there is no universal means, applicable to all molecules, but a necessary adaptation to each molecule and to each of its therapeutic uses.

SUMMARY OF THE INVENTION

For alfuzosin, we have carried out a systematic experimental search of solvents, excipients and absorption promoters and very particularly of their combinations which contribute to making it possible to improve transdermal passage. We have found that certain organic solvents and certain aliphatic compounds, and especially their optimum combinations, make possible a sufficient transdermal passage of alfuzosin to produce plasma levels which satisfy the criteria listed above.

This search was initially carried out on an "ex-vivo" model using human skin removed during plastic surgery operations and carefully preserved to guarantee that its physiological properties are maintained. Such a model was described by T. J. Franz (Current Problems in Dermatology, 7,58–68, 1978) and by H. Durrheim et al. (Journal of Pharmaceutical Sciences, 69, 7, 781–786, 1980).

DESCRIPTION OF THE INVENTION

The invention provides a transdermal pharmaceutical preparation containing N-[3-[(4-amino-6,7-dimethoxy-2-quinazolinyl)methylamino]-propyl]tetrahydro-2-furancarboxamide or a salt thereof and a mixture composed of water, at least one organic solvent, such as ethanol, ethyl acetate or propylene glycol, and at least one absorption promoter, such as fatty acids or alcohols containing an aliphatic chain with 5 to 30 carbon atoms.

These aliphatic alcohols and acids can be saturated, unsaturated, branched or substituted. It concerns, for example and not exhaustively, valeric, caprylic, isovaleric, caproic, oenanthic, pelargonic, capric, lauric, myristic, palmitic, margaric, stearic, oleic, arachidic, behenic, lignoceric, cerotic, montanic and melissic compounds and their unsaturated or branched or alternatively substituted homologues.

According to the invention, the preferred absorption promoters are selected from oleic, caprylic and capric acids.

The absorption promoters can be used alone or in combination, in a proportion of 1 to 500% of the weight of alfuzosin.

The alfuzosin content can range from 5 to 100 mg per preparation.

Other excipients can be added to the preparation so as to produce the desired pharmaceutical form, such as an ointment, cream, gel, emulsion, transdermal device or stamp.

Finally, it may be necessary to introduce into the preparation a compound which corrects certain local side-effects of the preparation. In addition, it is possible to use, for example, hydrating agents (urea, sorbitol or similar polyols), calming agents (local anaesthetics, for example), anti-inflammatory agents (corticoids or NSAI) or anti-histamines.

The transdermal preparation can consist of a matrix system, a reservoir system or a system consisting of successive coatings. In all cases, the system includes alfuzosin or a salt thereof, the promoter(s), technological excipients and the corrective compound(s) described above. The transdermal preparation can additionally include suitable constituents for producing the system, ensuring its preservation and enabling it to be used.

These constituents can be divided into three groups: passive supports, active constituents of the system, and adhesives.

The passive support can be a metal film, for example of aluminium, a fabric or a non-woven network of natural or artificial fibres, a polymeric film such as polyethylene, polypropylene, polytetrafluoroethylene, cellulose polymer, acrylic polymer, vinyl polymer, silicone polymer or an acrylonitrile polymer.

The active constituents of the system can be polymeric films or matrices such as: polyethylene, polypropylene, polytetrafluoroethylene, cellulose polymer, acrylic polymer, vinyl polymer, silicone polymer or acrylonitrile polymer.

The adhesive(s) can consist of natural or synthetic rubber, polyisobutylene, polyacrylates or poly(vinyl ether).

The transdermal pharmaceutical preparation of alfuzosin according to the invention is characterized in that, after its application to human skin, the therapeutic effects of the alfuzosin are obtained in a stable, continuous and sustained fashion.

According to the invention, it is possible to obtain the transdermal preparations in the following way:

Propylene glycol and oleic acid are mixed in proportions such that their total content represents 4 to 15% (m/m) of the final preparation.

This mixture is dispersed, in the absence of air and with strong stirring, in 4 to 9% (m/m) of ultrapure water and then 2 to 7% (m/m) of a viscosifying agent (colloidal silica, for example) are incorporated.

This pre-emulsion is then mixed with an aqueous dispersion of a neutral copolymer based on polyacrylates and polymethacrylates, in the absence of air and with slow stirring, in the proportion of 59 to 89.5% (m/m).

Alfuzosin (base) is suspended in the preparation at a concentration of 0.5 to 10% (m/m), in the absence of air and with very strong stirring.

The preparation is spread over a cold-hammered aluminium film (with a thickness of 30 µm, for example) coated with polyethylene on the face receiving the preparation in such a way that, for a given surface area, the volume of preparation contains an amount of active principle which is sufficient for its release kinetics.

Drying and polymerisation are carried out in a ventilated oven.

The preparation is coated with a fatty acid polyaminoacrylate adhesive in aqueous solution, in an amount sufficient to provide suitable adhesion for 24 hours.

Drying is carried out in a ventilated oven.

A protective film is applied to the adhesive face.

The transdermal systems are packaged in impermeable and opaque sealed sachets.

We claim:

1. A pharmaceutical preparation for transdermal administration, which preparation comprises alfuzosin [N-[3-[(4-amino-6,7-dimethoxy-2-quinazolinyl)methylamino]propyl]-tetrahydro-2-furancarboxamide] or a salt thereof, and a mixture composed of water, at least one organic solvent, and at least one absorption promoter, wherein the amount of alfuzosin is from 5 to 100 mg per unit dose and wherein the proportion of said absorption promoter is from 1 to 500% of the weight of alfuzosin.

2. A pharmaceutical preparation according to claim 1, wherein the organic solvent is selected from the group consisting of ethanol, ethyl acetate and propylene glycol.

3. A pharmaceutical preparation according to claim 1, wherein the absorption promoter is selected from the group consisting of fatty acids and alcohols containing an aliphatic chain with 5 to 30 carbon atoms.

\* \* \* \* \*